(12) United States Patent  
Levine

(10) Patent No.: US 9,826,924 B2  
(45) Date of Patent: Nov. 28, 2017

(54) HEARING ASSESSMENT METHOD AND SYSTEM

(71) Applicant: dB Diagnostic Systems, Inc., Weston, CT (US)

(72) Inventor: Steven Brian Levine, Weston, CT (US)

(73) Assignee: dB Diagnostic Systems, Inc., Weston, CT (US)

( * ) Notice: Subject to any disclaimer, the term of this patent is extended or adjusted under 35 U.S.C. 154(b) by 42 days.

(21) Appl. No.: 14/190,924

(22) Filed: Feb. 26, 2014

(65) Prior Publication Data

US 2014/0243702 A1     Aug. 28, 2014

Related U.S. Application Data

(60) Provisional application No. 61/769,449, filed on Feb. 26, 2013.

(51) Int. Cl.  
    *A61B 5/12*          (2006.01)

(52) U.S. Cl.  
CPC ............. *A61B 5/123* (2013.01); *A61B 5/12* (2013.01); *A61B 5/126* (2013.01)

(58) Field of Classification Search  
CPC ........... A61B 5/12; A61B 5/121; A61B 5/123; A61B 5/125; A61B 5/126  
USPC ............ 600/559; 381/58, 60, 23.1; 73/585  
See application file for complete search history.

(56) References Cited

U.S. PATENT DOCUMENTS

| | | | |
|---|---|---|---|
| 5,197,332 A | 3/1993 | Shennib | |
| 5,645,074 A | 7/1997 | Shennib et al. | |
| 5,916,174 A | 6/1999 | Dolphin | |
| 5,935,060 A * | 8/1999 | Iliff | G06F 19/322 600/300 |
| 6,167,138 A * | 12/2000 | Shennib | A61B 5/121 381/23.1 |
| 6,379,314 B1 | 4/2002 | Horn | |
| 6,964,642 B2 | 11/2005 | Wasden et al. | |
| 6,974,421 B1 | 12/2005 | Causevic et al. | |
| 7,018,342 B2 | 3/2006 | Harrison et al. | |
| 7,037,274 B2 | 5/2006 | Thornton et al. | |
| 7,132,949 B2 | 11/2006 | Harrison et al. | |
| 7,288,071 B2 | 10/2007 | Harrison et al. | |
| 7,288,072 B2 | 10/2007 | Stott et al. | |
| 7,465,277 B2 | 12/2008 | Wasden et al. | |

(Continued)

FOREIGN PATENT DOCUMENTS

| | | |
|---|---|---|
| CN | 104856689 A | 8/2015 |
| CN | 203244396 U | 8/2015 |

(Continued)

OTHER PUBLICATIONS

"Recommended Procedure—Tympanometry", the British Society of Audiology, 2013.*

(Continued)

*Primary Examiner* — Matthew Kremer

(74) *Attorney, Agent, or Firm* — Lisa J. Moyles; Janelle A. Bailey

(57) ABSTRACT

A system and a method for a healthcare provider to easily, accurately and efficiently provide a hearing test and a pressure test, i.e., a hearing assessment, for their patients, in a way that accurately detects hearing loss and provides recommendations for seeking further assistance from qualified hearing health specialists is provided.

16 Claims, 2 Drawing Sheets

(56) References Cited

U.S. PATENT DOCUMENTS

| | | | |
|---|---|---|---|
| 7,695,441 B2 | 4/2010 | Harrison et al. | |
| 7,854,704 B2 | 12/2010 | Givens et al. | |
| 8,394,032 B2* | 3/2013 | Cromwell et al. | 600/559 |
| 8,447,042 B2 | 5/2013 | Gurin | |
| 8,968,209 B2 | 3/2015 | Van Tasell | |
| 8,983,084 B2 | 3/2015 | Bengtsson | |
| 2001/0023360 A1* | 9/2001 | Nelson | A61B 5/0031 607/60 |
| 2001/0037220 A1* | 11/2001 | Merry | A61B 5/0002 705/3 |
| 2003/0078515 A1 | 4/2003 | Menzel et al. | |
| 2004/0006283 A1 | 1/2004 | Harrison et al. | |
| 2004/0024328 A1* | 2/2004 | Tabbara | A61B 5/7475 600/523 |
| 2004/0039299 A1 | 2/2004 | Harrison et al. | |
| 2004/0073136 A1* | 4/2004 | Thornton | A61B 5/12 600/559 |
| 2004/0152998 A1 | 8/2004 | Stott et al. | |
| 2005/0124375 A1 | 6/2005 | Nowosielski | |
| 2006/0074341 A1* | 4/2006 | Causevic | A61B 5/121 600/561 |
| 2006/0173246 A1* | 8/2006 | Zaleski | G06F 19/322 600/300 |
| 2007/0128174 A1* | 6/2007 | Kleinsek | A61K 35/12 424/93.7 |
| 2007/0219458 A1 | 9/2007 | Jeng | |
| 2008/0121038 A1 | 5/2008 | Davis | |
| 2008/0243005 A1* | 10/2008 | Jung | A61B 5/16 600/481 |
| 2009/0177113 A1* | 7/2009 | Cromwell | A61B 5/121 600/559 |
| 2010/0167801 A1* | 7/2010 | Karkanias | A61B 5/0022 463/7 |
| 2010/0191143 A1 | 7/2010 | Ganter et al. | |
| 2010/0268115 A1 | 10/2010 | Wasden et al. | |
| 2010/0303249 A1 | 12/2010 | Semcken | |
| 2011/0009770 A1* | 1/2011 | Margolis | A61B 5/121 600/559 |
| 2011/0034827 A1 | 2/2011 | Rix | |
| 2011/0110528 A1 | 5/2011 | Latzel | |
| 2011/0190658 A1 | 8/2011 | Sohn et al. | |
| 2011/0257994 A1 | 10/2011 | Givens et al. | |
| 2012/0029383 A1 | 2/2012 | Henriksen et al. | |
| 2012/0130271 A1 | 5/2012 | Margolis et al. | |
| 2012/0157876 A1 | 6/2012 | Bang et al. | |
| 2012/0282976 A1 | 11/2012 | Suhami | |
| 2013/0023787 A1 | 1/2013 | Dowd | |
| 2013/0303940 A1 | 11/2013 | Saly | |
| 2014/0153727 A1* | 6/2014 | Walsh et al. | 381/58 |

FOREIGN PATENT DOCUMENTS

| | | |
|---|---|---|
| EP | 1353529 A1 | 4/2002 |
| EP | 2521377 A1 | 11/2012 |
| EP | 2942009 A1 | 11/2015 |
| WO | WO-2016024170 A1 | 2/2016 |

OTHER PUBLICATIONS

"Dianostic Evaluation", www.utdallas.edu/~thib/rehabinfo/de.htm, posted Feb. 12, 2001, printed Aug. 31, 2007, 4 pages.*
Hanks, Wendy D. et al., "Practical Tympanometry for Providers of Pediatric Health Care", Mar. 2, 2010, 30 pages.*
Onusko, Edward, "Tympanometry", American Family Physician, vol. 70, No. 9, Nov. 1, 20104, p. 1713-1720.*
Ototronix Diagnostics, Otogram Hearing Diagnostic System, Web Page URL: www.ototronixdiagnostics.com/otogram.html (printed Feb. 1, 2012).
NHS, Hearing tests—How they're performed, Web Page URL: www.nhs.uk/conditions/hearing-tests/pages/how it is performed . . . (printed Jan. 21, 2013).
GN Otometrics, Insights in Practice, Robert H. Margolis, Ph.D. & Donald E. Morgan, Ph.D., The Value of Automated Audiometry, Jan. 2008.
American Speech Language Hearing Association, Audiology Information Series, Identifying and Managing Hearing Loss in School-Age Children, 2001.
Otovation, Amplitude T-Series Brochure, 2007.

* cited by examiner

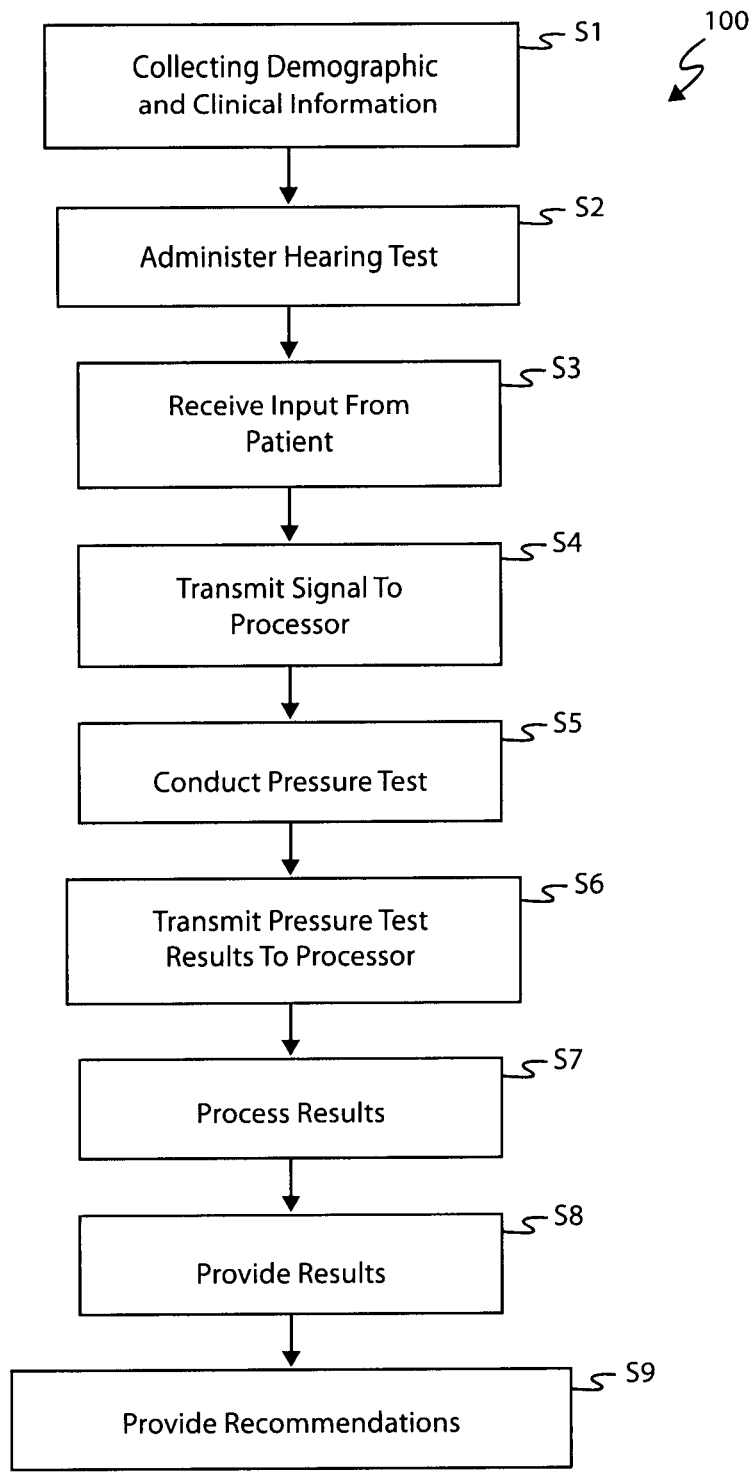

HEARING ASSESSMENT METHOD AND SYSTEM

CROSS-REFERENCE TO RELATED APPLICATIONS

This application claims the benefit of U.S. Provisional Application No. 61/769,449, filed Feb. 26, 2013.

FIELD

A method, system and computer-readable medium is generally described for diagnosing hearing loss and recommending treatment, particularly for use by healthcare providers who do not have expertise in disorders of the ear and/or hearing.

BACKGROUND

The incidence of hearing loss in the United States was 266 per thousand households in 1989, 283 per thousand in 2004, and 295 per thousand in 2008. In 2008, 43.25 million reported hearing difficulty. Between 2004 and 2008, the hearing impaired population grew 8.8% compared to a 4.5% increase in US households. Furthermore, the percent of the population that acknowledged a hearing loss grew from 10% in 1989 to 11.3% in 2008.

People with hearing loss rarely acknowledge the disorder. From the time hearing loss is first noticed, the average hearing impaired person delays seven years before seeking assistance. Reasons given by some are they may not believe that they can afford a hearing aid, so they don't inquire about a hearing analysis. Others fear ridicule and taunting by family and friends if they use a hearing aid. And yet for others, acknowledging hearing loss means they have to acknowledge that they are aging and that their bodies are simply not able to do things they once took for granted.

Technology used in hearing aids is improving rapidly in a manner parallel to other chip-based consumer goods. Newest technologies remain relatively expensive, but slightly older technologies are more affordable. Furthermore, continuous improvement has been made in designs to make hearing aids less cumbersome and noticeable in the ear along with better ability to eliminate background or undesirable noise. So many more people would benefit from hearing assistance than those currently seeking such care.

Moreover, many people might typically seek advice from a physician or other healthcare provider to provide at least some guidance on the matter, but most are not prepared to provide such guidance. Current tools for performing hearing tests available to the healthcare professionals at large remain expensive and labor intensive relative to reimbursement for such tests. Furthermore, if under such conditions a hearing disorder is identified, the patients are often not referred in an expeditious and efficient manner for diagnosis and/or treatment.

Thus, what is needed is a way to provide a hearing assessment by a wide range of healthcare providers who have not traditionally participated in hearing analysis, e.g. primary care physicians, pediatricians, neurologists, naturopath doctors, chiropractic doctors and the like, referred to herein as a general "healthcare provider" as distinguished from hearing health specialists described hereinbelow. There is a need, therefore, for a system, method and computer-readable medium that provides a simple, cost effective hearing assessment to be administered by the general healthcare provider. There is a further need to provide a simplified means for referral by the healthcare providers to a hearing health specialist (e.g. audiologists and otolaryngologists).

BRIEF DESCRIPTION

A system, method and computer-readable medium for a healthcare provider to easily, accurately and efficiently provide a pure tone hearing and a pressure test, i.e., a hearing assessment, for their patients, in a way that accurately detects hearing loss and provides recommendations for seeking further assistance from qualified hearing health specialists is provided.

BRIEF DESCRIPTION OF THE FIGURES

A more particular description of the system, method and computer-readable medium briefly described above will be rendered by reference to specific embodiments thereof that are illustrated in the appended drawings. Understanding that these drawings depict only typical embodiments and are not therefore to be considered to be limiting of its scope, exemplary embodiments will be described and explained with additional specificity and detail through the use of the accompanying drawings in which:

FIG. 2 represents method steps according to an embodiment.

Figure 1:
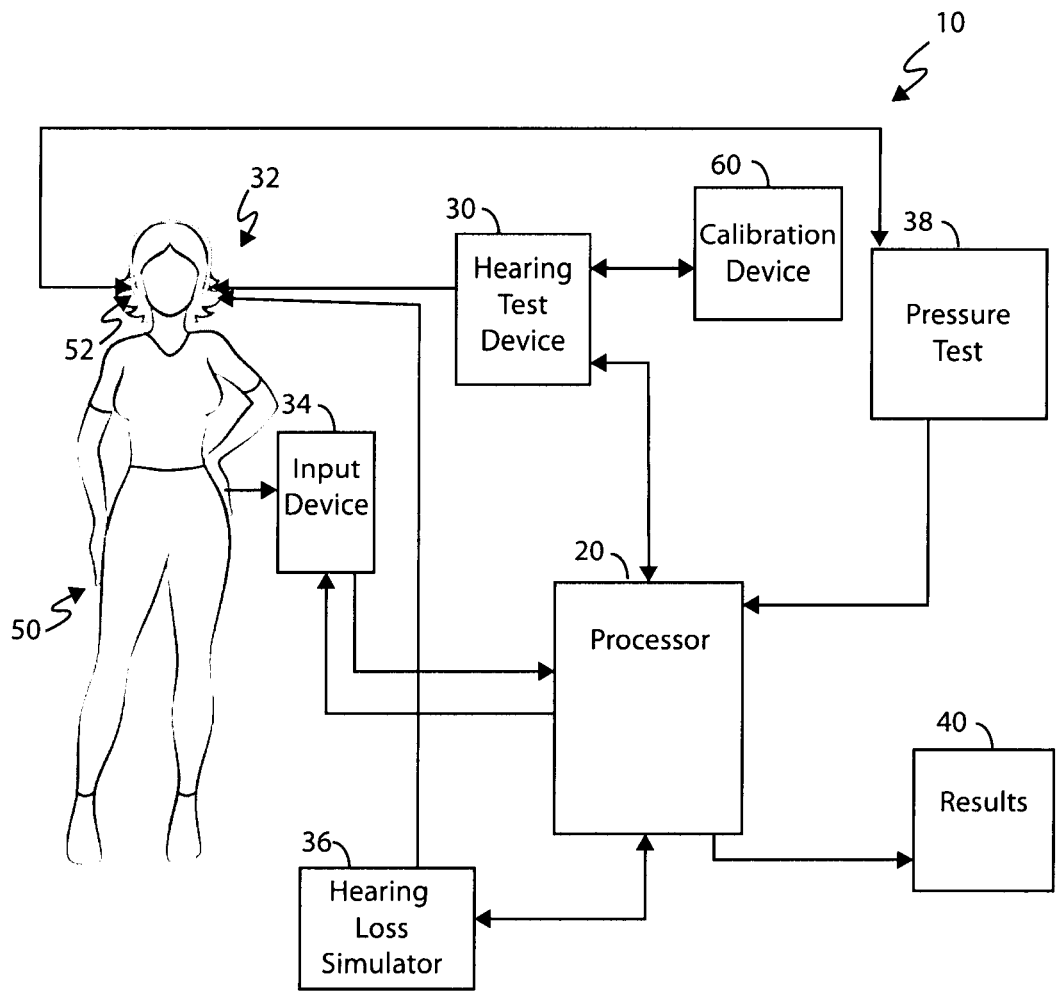
FIG. 1 schematically illustrates an embodiment in which the patient's hearing is assessed.

Various features, aspects, and advantages of the embodiments will become more apparent from the following detailed description, along with the accompanying figures in which like numerals represent like components throughout the figures and text. The various described features are not necessarily drawn to scale, but are drawn to emphasize specific features relevant to embodiments.

DETAILED DESCRIPTION

Reference will now be made in detail to embodiments. Each example is provided by way of explanation, and is not meant as a limitation and does not constitute a definition of all possible embodiments.

In an embodiment, a system, including various devices and/or mechanisms, a method and computer-readable medium for administration of a hearing assessment, including a hearing and pressure test, by a healthcare provider, is provided. As used herein, a "healthcare provider" is a provider of healthcare services that is not a hearing health specialist; the healthcare provider is e.g., a primary care physician, pediatrician, neurologist, naturopath doctor, chiropractic doctor and the like, while a "hearing health specialist" includes for example audiologists and otolaryngologists. By "interactive", what is meant is of or pertaining to a two-way system of electronic communications by means of a computer. By "portable", what is meant is capable of being easily carried or conveyed by hand. The configuration described herein is capable of providing a "hearing assessment", an assessment of the person's sense of hearing that is not quite as rigorous as a traditional, full-blown hearing test performed by an audiologist or other hearing health specialist using an audiometer, but includes a pressure test and is sufficient to provide at least a baseline indication of hearing issues so that the patient can be referred to a hearing health specialist for further analysis.

Now referring to FIG. 1 and according to an embodiment, a machine, kit or system 10 to enable a healthcare provider to administer a portable interactive hearing assessment to a patient or test subject 50 is illustrated. As shown herein, each of the devices/mechanisms/modules operable to conduct the hearing test are shown as separate individual parts, although it would be understood by one of ordinary skill in the art that one or more of the parts could be combined into a single device as described in more detail below.

Software/modules forming at least a portion of a platform for conducting the hearing test could be downloaded onto an input/interface device 34 such as a personal or laptop computer, or onto any device, such as a hand-held mobile digital electronic portable device, a tablet, a telephone, or the like, whether or not such devices have internet access. In another embodiment, the platform is made available to users via cloud computing. As used herein, the term "cloud computing" refers to when tasks are assigned to a combination of connections, software, and services, accessed over a network. The network of servers and connections is collectively known as "the cloud." Computing at the scale of the cloud allows users to access supercomputer-level power from a portable electronic device. Using an access point like an iPhone® or iPad® device, available from Apple, Inc., an Android® tablet available from Samsung, a Windows® 8 operating system available from Microsoft or a personal computer (PC) using Windows® 8 operating system from any PC manufacturer, users can reach into the cloud for resources as they need them. It would be understood by one of ordinary skill in the art that software can be provided that is compatible with Android (an operating system based on Linux), Apple® iOS and Windows® 8 operating systems as well so that a thin client may be adapted for a variety of environments. Alternatively, various applications could simply be hosted or housed upon the device.

As shown in FIG. 1, the patient 50 is provided with the input device 34, and is requested to respond to one or more questions designed to solicit background information about the patient. Such background information includes but is not limited to identifying demographic data and clinical history pertinent to issues surrounding the ear, hearing and balance. The input device 34 may include, for example, a display (including e.g. a touch screen), a keyboard, a mouse or other pointing device, a switch/button, and componentry capable of providing output through the display, a speaker, and/or a printer, and is in communication with a processor 20 (as described in more detail below).

In the embodiment of FIG. 1, a hearing test device 30 is configured to administer the hearing test by transmitting as sound at least four distinct pure tone frequencies (250 Hz, 500 Hz, 1000 Hz, and 2000 Hz) at varying sound levels to the patient 50, in a way that repeatedly measures a threshold for each ear of the patient. By "threshold" what is meant is the methodology of providing varying levels of loudness to identify a level of hearing perceived by the patient. For instance, as a starting point, a higher threshold sound is transmitted to the patient, and the patient indicates that the sound has been received (as discussed in greater detail below). Then, the threshold is dropped to a level of loudness that would normally be considered too low for hearing, and the threshold is gradually raised until the patient once again indicates that the sound has been heard. Then, the threshold is lowered once again, and gradually raised until the patient once again indicates hearing. The threshold level is recorded accordingly to measure the level of hearing of the patient.

As shown in FIG. 1, the sounds are sent to a headset 32 worn by the patient 50, and the headset 32 is shown with a wired connection to the hearing test device 30. In a preferred embodiment, the headset 32 is a Sennheiser HDA300 audiometer headphone.

In order to withstand rigor under US Food and Drug Administration procedures, and more importantly to qualify as an event that is reimbursable under personal health insurance plans, the hearing test device 30 must provide the hearing test in a repeatable, calibrated way. In other words, the hearing test device 30 is capable of being calibrated and tested for calibration from time to time as necessary so that the various frequency tones and loudness of those tones are uniform across all devices. As shown herein, the hearing test device 30 interacts with a calibration device 60 as necessary for calibration.

Upon hearing the varying sound levels of the at least four pure tone frequencies, the patient 50 responds to the lowest sound level they can identify by activating the input device 34. In other words, the patient responds upon hearing the sounds, those sounds they can actually hear, by providing input to the input device 34.

In an embodiment, the input device 34 and the hearing test device 30 are integrated into a single unit. In such an embodiment, the hearing test device 30 is actually an application housed on the input device 34. As would be understood by one of ordinary skill in the art, activation of the input device could be performed in many ways. In an embodiment, a switch/button may be activated, and in another embodiment, the patient simply provides a finger click on the screen of the tablet or iPad device. In the embodiment where a button is used, such a device could be wired to the input device 34 (not shown) as would be understood by one of ordinary skill in the art.

In any event, a signal is transmitted to a processor 20 indicative of the patient's response. The processor 20 is configured to process and issue signals associated with the hearing test and to receive the response from the patient based on the patient's ability to hear each of the at least four pure tone frequencies. As described above for the hearing test device, the processor may similarly be housed on a portable device, such as an iPad. In any event, once the results of the hearing test are processed by the processor 20, the results are transmitted to a simulator 36, which is configured to visually display the loss and audibly demonstrate the effects of the loss measured by the hearing test. In short, the processor 20 sends a signal indicative of whether or not the patient's hearing is considered normal or abnormal.

In an embodiment, the simulator 36 displays the following information to the patient and/or healthcare provider:

If a hearing loss is indicated that is of a high frequency hearing loss, the hearing loss simulator 36 will demonstrate to the patient what can be heard from, for instance, a child as if their hearing is normal, as compared to what the patient is currently hearing. The demonstration via the simulator 36 can be repeated as necessary for the patient, the healthcare provider, and/or anyone accompanying the patient, like a spouse, parent or child, so that the other person can get a sense for what the patient is not hearing . . . in other words, the scope of their hearing loss.

If a hearing loss is indicated that is of a low frequency, a similar demonstration can be made to that of the high frequency hearing loss discussed above, using a man's voice, which is usually deeper in timber and having a low frequency of sound. For all other types of hearing loss, a demonstration may be made to the patient of what can be heard from a woman if their hearing is normal, as compared to what the patient him/herself is hearing. Of course, any of these results are capable of being repeated for the patient and/or anyone else having an interest in the results of the hearing test.

If the hearing test is determined to be abnormal, then an additional test will be conducted in the form of a pressure test 38. In an embodiment, a tympanometer is provided that is configured to conduct a middle ear compliance test as the pressure test 38 of at least one ear 52 of the patient 50. Tympanometry is an examination used to test the condition of the middle ear and mobility of the eardrum (tympanic membrane) and the conduction bones by creating an air pressure variation of the ear canal. The pressure test 38 provides an objective means of testing the middle-ear functions and should be viewed in conjunction with the pure tone audiometry for an overall test of hearing. In evaluating hearing loss, tympanometry permits a distinction between the presence or absence of middle ear interference with respect to a measured hearing loss. Furthermore, in a primary care setting, a tympanometer is typically already useful for diagnosing otitis media by demonstrating the presence of a middle ear effusion. In any event, the tympanometer is configured to transmit a signal indicative of results of the pressure test 38 to the processor 20.

Upon receipt of the patient's response to the hearing test described above and also of the pressure test results, the processor 20 provides the results 40 of the assessment to the healthcare provider so that the patient may be referred to an appropriate hearing health specialist as required. In an embodiment, the results 40 include a report and recommendation regarding the patient's hearing, which can be provided in a display and/or a printed report. If no hearing loss is detected, the system may simply provide the results 40 as a printed report for either or both of the physician and patient. If a symmetrical hearing loss is detected from the hearing test, and the results 40 of the pressure test 38 is normal bilaterally, and a physical exam of the ear is normal bilaterally, the processor 20 is capable of recommending referral to an audiologist. For all other combinations of results 40, a referral to an otolaryngologist will be generated.

In yet a further embodiment, a listing of qualified hearing health specialists could be stored in a database, (not specifically shown), housed either on the processor 20 itself, or accessible by the internet to a cloud-based database, so that proper referrals can be made. Such a database could be maintained by the healthcare provider, or more preferably, maintained based on qualifying criteria so that referrals may be made with confidence.

At least one advantage of the system 10 and method 100 described herein is that the system 10 is given automatic credibility since it is being administered by another healthcare provider—one that is already in a relationship with the patient 50 that is engendered with trust and confidence—but that is not considered a hearing specialist. Another advantage is the widespread distribution of the system 10 and method 100 that enables engagement of the healthcare community as a whole, not just those already in the business of testing, assessing, analyzing and diagnosing hearing problems, but rather expands to providers that have not traditionally been equipped to help in diagnosing this problem that plagues so many patients.

With reference to FIG. 2, and with reference to the typical components described hereinabove, a computer-implemented method 100 according to an aspect to enable a healthcare provider to provide an automatic interactive patient hearing assessment is illustrated. By "automatic", what is meant is that at least a portion of the method is conducted with little or no direct human control. For instance, the patient 50 is simply outfitted with the headset 32 and provided with the input/interface device 34 like a tablet or PDA that has been configured with the various modules discussed in detail above. And once, the "start" button has been activated, the only input required is that received directly from the patient 50 in the form of responses to the request for demographic information and indicative of hearing. Thus, the processor 20 simply automatically runs through the software routine without additional input from the healthcare provider.

The method 100 is conducted on a processor 20, and may include one or more of the steps of: collecting demographic and clinical information S1, administering a hearing test by transmitting as sound at least four pure tone frequencies to a patient, S2; receiving a signal indicative of the patient's response based on the patient's ability to hear each of the at least four pure tone frequencies, S3, and transmitting the signal to the processor, S4; conducting a pressure test of at least one ear of the patient, S5; transmitting a signal indicative of the results of the pressure test to the processor, S6; processing signals associated with the hearing test and the pressure test, S7; visually displaying and/or audibly demonstrating the effects of the loss measured by the hearing test, S8; and reporting recommendations regarding the patient's hearing, S9.

In yet another embodiment, a non-transitory computer-readable medium to store a program for controlling the processor 20 to automatically and interactively assess hearing of a patient by a healthcare provider is provided to execute the method steps set out above. The program may be stored in a compressed, uncompiled and/or encrypted format. The program may furthermore include other program elements, such as an operating system, a database management system, and/or device drivers used by the processor 20 to interface with other peripheral devices.

The processor 20 may perform instructions of the program, and thereby operates in accordance with the present embodiments. For example, the processor 20 may generate and administer the hearing test and receive the input from the patient, and once the processor 20 receives the pressure test results, process the various data inputs and provide results of the hearing assessment in the form of a hearing loss simulation and/or printed results.

The system components, methods and computer-readable medium illustrated are not limited to the specific embodiments described herein, but rather, features illustrated or described as part of one embodiment can be used on or in conjunction with other embodiments to yield yet a further embodiment. It is intended that the system and method include such modifications and variations. Further, steps described in the method may be utilized independently and separately from other steps described herein.

While the system and method has been described with reference to a preferred embodiment, it will be understood by those skilled in the art that various changes may be made and equivalents may be substituted for elements thereof without departing from the spirit and scope thereof and the following claims. In addition, many modifications may be made to adapt a particular situation or material to the teachings herein without departing from the essential scope thereof.

Embodiments can be implemented in digital electronic circuitry, or in computer hardware, firmware, software, or in combinations thereof. Apparatus can be implemented in a computer program product tangibly embodied or stored in a machine-readable storage device or non-transitory computer-readable medium as discussed hereinabove for execution by the programmable processor; and method actions can be performed by the programmable processor executing a program of instructions to perform functions by operating on input data and generating output. The method can be implemented advantageously in one or more computer programs that are executable on a programmable system including the at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired; and in any case, the language can be a compiled or interpreted language.

Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD_ROM disks. Any of the foregoing can be supplemented by, or incorporated in, ASICs (application-specific integrated circuits).

In this specification and the claims that follow, reference will be made to a number of terms that have the following meanings. The singular forms "a," "an" and "the" include plural referents unless the context clearly dictates otherwise. Furthermore, references to "one embodiment" are not intended to be interpreted as excluding the existence of additional embodiments that also incorporate the recited features. Approximating language, as used herein throughout the specification and claims, may be applied to modify any quantitative representation that could permissibly vary without resulting in a change in the basic function to which it is related.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable, or suitable. For example, in some circumstances an event or capacity can be expected, while in other circumstances the event or capacity cannot occur—this distinction is captured by the terms "may" and "may be."

As used in the claims, the word "comprises" and its grammatical variants logically also subtend and include phrases of varying and differing extent such as for example, but not limited thereto, "consisting essentially of" and "consisting of."

Advances in science and technology may make equivalents and substitutions possible that are not now contemplated by reason of the imprecision of language; these variations should be covered by the appended claims. This written description uses examples to disclose embodiments, including the best mode, and also to enable any person of ordinary skill in the art to practice the embodiments, including making and using any devices or systems and performing any incorporated methods. The patentable scope of the embodiments is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A system to enable a healthcare provider to administer a portable interactive patient hearing assessment, the system comprising:
    a hand-held, mobile hearing test device for administration of a threshold hearing test by the healthcare provider, the hearing test device configured to transmit at least four distinct pure tone frequencies to a patient;
    a hand-held, mobile input device configured for activation by the patient upon hearing the at least four pure tone frequencies, and for transmitting one or more signals to a processor indicative of the patient's response to the hearing test in response to the patient's activation of the mobile input device, wherein the processor is configured to
    (i) process the one or more signals indicative of the patient's response to the hearing test,
    (ii) issue one or more hearing test result signals based on the one or more signals indicative of the patient's response to the hearing test which is based on the patient's ability to hear each of the at least four pure tone frequencies and
    (iii) process the hearing test result signals to determine the patient's hearing results; and
    a tympanometer configured to conduct a pressure test of each ear of the patient, the tympanometer configured to indicate pressure test results,
    wherein upon receipt of the one or more signals indicative of the patient's response to the hearing test and the pressure test results, the processor provides a report and recommendation based on the pressure test results and the patient's hearing results, wherein
    (i) when the patient's hearing results indicate no hearing loss, the report is provided to the healthcare provider and/or to the patient,
    (ii) when the patient's hearing results indicate a hearing loss, the pressure test results are normal bilaterally, and an input by the healthcare provider to the system that a physical exam of the patient's ears indicates that the ears are normal bilaterally, the report and the recommendation comprise a referral to an audiologist, and
    (iii) when the patient's hearing results indicate a hearing loss and when the pressure test results are not normal bilaterally and/or an input by the healthcare provider to the system that the physical exam of the patient's ears indicates that the ears are not normal bilaterally, the report and the recommendation comprise a referral to an otolaryngologist.

2. The system of claim 1, further comprising a calibration device configured to calibrate the hand-held, mobile hearing test device for uniformity of the at least four pure tone frequencies.

3. The system of claim 1, further comprising a simulator configured to demonstrate effects of the hearing loss, in an audible manner, measured by the hearing test to a person accompanying the patient so that the accompanying person understands a scope of the patient's hearing loss.

4. The system of claim 3, wherein the hand-held, mobile input device is a portable electronic device configured to host a plurality of modules, wherein the modules comprise the hand-held, mobile hearing test device, the processor and the simulator.

5. The system of claim 3, wherein the hand-held, mobile input device is a portable electronic device configured to access a plurality of modules via cloud computing, wherein the modules comprise the hand-held, mobile hearing test device, the processor and the simulator.

6. The system of claim 1, wherein the hand-held, mobile input device is further configured to collect demographic information identifying the patient and answers to a series of questions pertinent to clinical history surrounding ear issues, hearing and balance of the patient.

7. A system to enable a healthcare provider to administer a portable interactive patient hearing assessment, the system comprising:
  a hand-held, mobile hearing test device for administration of a threshold hearing test by a healthcare provider, the hearing test device configured to transmit at least four distinct pure tone frequencies to a patient;
  a hand-held, mobile input device configured for activation by the patient upon hearing the at least four pure tone frequencies, and for transmitting one or more signals to a processor indicative of the patient's response to the hearing test in response to the patient's activation of the mobile input device, wherein the processor is configured to
  (i) process the one or more signals indicative of the patient's response to the hearing test,
  (ii) issue one or more hearing test result signals based on the one or more signals indicative of the patient's response to the hearing test which is based on the patient's ability to hear each of the at least four pure tone frequencies, and
  (iii) process the hearing test result signals to determine the patient's hearing results;
  a simulator configured to, in a case that the patient's ability to hear indicates a hearing loss, demonstrate effects of the hearing loss, in an audible manner, measured by the hearing test to a person accompanying the patient so that the accompanying person understands a scope of the patient's hearing loss; and
  a tympanometer configured to conduct a pressure test of each ear of the patient, the tympanometer configured to indicate pressure test results,
  wherein upon receipt of the one or more signals indicative of the patient's response to the hearing test and the pressure test results, the processor provides a report and recommendation based on the patient's hearing results and the pressure test results, wherein
  (i) when the patient's hearing results indicate no hearing loss, the report is provided to the healthcare provider and/or to the patient,
  (ii) when the patient's hearing results indicate a hearing loss, the pressure test results are normal bilaterally, and a result entered in the system by the healthcare provider that a physical exam of the patient's ears indicates that the ears are normal bilaterally, the report and the recommendation comprise a referral to an audiologist, and
  (iii) when the patient's hearing results indicate a hearing loss and when the pressure test results are not normal bilaterally and/or a result entered in the system by the healthcare provider that the physical exam of the patient's ears indicates that the ears are not normal bilaterally, the report and the recommendation comprise a referral to an otolaryngologist.

8. The system of claim 7, further comprising a calibration device configured to calibrate the hand-held, mobile hearing test device for uniformity of the at least four pure tone frequencies.

9. The system of claim 7, wherein the hand-held, mobile input device is further configured to collect demographic information identifying the patient and answers to a series of questions pertinent to clinical history surrounding ear issues, hearing and balance of the patient.

10. The system of claim 7, wherein the hand-held, mobile input device is a portable electronic device configured to host a plurality of modules, wherein the modules comprise the hand-held, mobile hearing test device, the processor and the simulator.

11. The system of claim 7, wherein the hand-held, mobile input device is a portable electronic device configured to access a plurality of modules via cloud computing, wherein the modules comprise the hand-held, mobile hearing test device, the processor and the simulator.

12. A system to enable a healthcare provider to administer a portable interactive patient hearing assessment, the system comprising:
  a hand-held, mobile hearing test device for administration of a threshold hearing test by a healthcare provider, the hearing test device configured to transmit at least four distinct pure tone frequencies to a patient;
  a hand-held, mobile input device configured to collect demographic information identifying the patient and for activation by the patient upon hearing the at least four pure tone frequencies, and for transmitting one or more signals to a processor indicative of the patient's response to the hearing test in response to the patient's activation of the mobile input device, wherein the processor is configured to
  (i) process the one or more signals indicative of the patient's response to the hearing test,
  (ii) issue one or more hearing test result signals based on the one or more signals indicative of the patient's response to the hearing test which is based on the patient's ability to hear each of the at least four pure tone frequencies, and
  (iii) process the hearing test result signals to determine the patient's hearing results;
  a simulator configured to, in a case that the patient's ability to hear indicates a hearing loss, demonstrate effects of the hearing loss, in an audible manner, measured by the hearing test to a person accompanying the patient so that the accompanying person understands a scope of the patient's hearing loss; and
  a tympanometer configured to conduct a pressure test of each ear of the patient, the tympanometer configured to indicate pressure test results,
  wherein upon receipt of the one or more signals indicative of the patient's response to the hearing test and the pressure test results, the processor provides a report and recommendation based on the patient's hearing results and the pressure test results, wherein
  (i) when the patient's hearing results indicate no hearing loss, the report is provided to the healthcare provider and/or to the patient,
  (ii) when the patient's hearing results indicate a hearing loss, the pressure test results are normal bilaterally, and an input by the healthcare provider to the system that a physical exam of the patient's ears indicates that the ears are normal bilaterally, the report and the recommendation comprise a referral to an audiologist, and (iii) when the patient's hearing results indicate a hearing loss and when the pressure test results are not normal bilaterally and/or an input by the healthcare provider to the system that the physical exam of the patient's ears indicates that the ears are not normal bilaterally, the report and the recommendation comprise a referral to an otolaryngologist.

13. The system of claim 12, further comprising a calibration device configured to calibrate the hand-held, mobile hearing test device for uniformity of the at least four pure tone frequencies.

14. The system of claim 12, wherein the hand-held, mobile input device is further configured to collect answers to a series of questions pertinent to clinical history surrounding ear issues, hearing and balance of the patient.

15. The system of claim 12, wherein the hand-held, mobile input device is a portable electronic device configured to host a plurality of modules, wherein the modules comprise the hand-held, mobile hearing test device, the processor and the simulator.

16. The system of claim 12, wherein the hand-held, mobile input device is a portable electronic device configured to access a plurality of modules via cloud computing, wherein the modules comprise the hand-held, mobile hearing test device, the processor and the simulator.

* * * * *